United States Patent
Chambard et al.

(10) Patent No.: US 8,536,082 B2
(45) Date of Patent: *Sep. 17, 2013

(54) DEHYDROGENATION CATALYST PREPARATION BY DRY IMPREGNATION

(75) Inventors: Alexandre Chambard, Javerlhac (FR); Yohan Oudart, Pantin (FR)

(73) Assignee: IFP Energies Nouvelles, Rueil-Mamaison Cedex (FR)

( * ) Notice: Subject to any disclaimer, the term of this patent is extended or adjusted under 35 U.S.C. 154(b) by 651 days.

This patent is subject to a terminal disclaimer.

(21) Appl. No.: 12/775,822

(22) Filed: May 7, 2010

(65) Prior Publication Data

US 2010/0285954 A1    Nov. 11, 2010

(30) Foreign Application Priority Data

May 7, 2009 (FR) ..................................... 09 02261

(51) Int. Cl.
*B01J 23/00* (2006.01)

(52) U.S. Cl.
USPC ........... 502/313; 502/227; 502/330; 502/339; 502/300; 502/325; 502/326; 502/328; 502/329; 502/229

(58) Field of Classification Search
None
See application file for complete search history.

(56) References Cited

U.S. PATENT DOCUMENTS

| 3,909,451 | A | | 9/1975 | Wilhelm | |
|---|---|---|---|---|---|
| 3,994,832 | A | | 11/1976 | Antos | |
| 4,914,075 | A | * | 4/1990 | Bricker et al. | 502/330 |
| 5,482,910 | A | * | 1/1996 | Bricker et al. | 502/300 |

FOREIGN PATENT DOCUMENTS

| EP | 0559519 A1 | 9/1993 |
|---|---|---|
| FR | 0902261 R | 12/2009 |

OTHER PUBLICATIONS

Institut National De La Propriete Industrielle. "Written Opinion." FR0902261. Applicant: IFP. Date of deposit: May 7, 2009.

* cited by examiner

*Primary Examiner* — Melvin C Mayes
*Assistant Examiner* — Smita Patel
(74) *Attorney, Agent, or Firm* — Millen, White, Zelano & Branigan, P.C.

(57) ABSTRACT

The invention relates to a method of preparing a dehydrogenation catalyst comprising a group VIII metal, a group IVA metal and a refractory oxide support. The method comprises stages of preparing the dry impregnation aqueous solution containing said group VIII metal, ammonia, either in solution or in gas form, and a complexing agent. It then comprises stages of aging the aqueous solution, of dry impregnation of the support, of maturing the impregnated support, of drying the impregnated support and of calcining the dried support.

21 Claims, No Drawings

DEHYDROGENATION CATALYST PREPARATION BY DRY IMPREGNATION

CROSS-REFERENCE TO RELATED APPLICATION

This application is related to concurrently filed application "REFORMING CATALYST PREPARATION BY DRY IMPREGNATION" by Yohan OUDART, U.S. application Ser. No. 12/774,480, filed May 5, 2010, claiming priority of FR 09/02.260 filed May 7, 2009, incorporated by reference herein.

FIELD OF THE INVENTION

The invention relates to the sphere of dehydrogenation of long paraffins in the presence of a catalyst prepared by means of an original method of dry deposition of platinum.

Alkenes are prime feeds for the petrochemical industry. The main alkene sources are steam cracking and catalytic cracking processes. However, these two processes also produce by-products and the increasing demand is directed towards specific alkenes whose production through cracking would be uneconomical.

The direct production of alkenes therefore remains indispensable in some instances. This is the case with propylene, isobutene or long-chain linear alkenes for production of polypropylene, MTBE and LAB (Linear Alkyl Benzene) respectively.

The main specific features of the dehydrogenation reaction lie in that thermodynamic equilibrium limits the conversion rate per pass and in that the reaction is highly endothermic. These two characteristics are determining for technological choices as regards the process, as well as catalyst design and forming.

Thus, the reaction of dehydrogenation of long n-paraffins comprising between 9 and 16 carbon atoms generally occurs at temperatures of approximately 450° C.-500° C., with a conversion rate per pass ranging between 10% and 25%, limited by thermodynamics.

Operating at high temperature is necessary to maintain a high conversion level (close to thermodynamic equilibrium), but these high temperatures also promote a certain number of parasitic reactions leading to a product of lower quality. Among these reactions, there are reactions leading to the formation of light products (acid cracking, hydrogenolysis), of highly unsaturated carbon deposit precursor and deactivation initiator (dehydrocyclization, deep dehydrogenation) compounds such as aromatic compounds or diolefins, and skeleton isomerization reactions responsible for the formation of branched molecules. Under such particularly severe operating conditions, it is very difficult to maintain a high activity and selectivity over long periods of time because of these side reactions.

The reaction of dehydrogenation of olefins to diolefins is a balanced reaction, faster than the conversion of paraffins to olefins. Production of diolefins is thus inevitable and it is highly correlated with the production of the desired olefins. On the other hand, it is known to the person skilled in the art that the production of cracked products and of aromatic compounds depends on the operating conditions, on the conversion, and also on the intrinsic selectivity of the active phase of the catalyst. Furthermore, dehydrogenation reactions being particularly fast, the presence of intragranular diffusion limitations is often difficult to avoid. This leads to an olefin and diolefin concentration enrichment at the core of the catalyst balls or extrudates, which causes a great increase in side reactions of aromatics and light compounds formation, or reactions of isomerization of paraffins and olefins to iso-paraffins and iso-olefins. These phenomena can be limited depending on the method, selection of the support, or on the way the active phase is deposited on this support.

The present invention relates to a group VIII metal deposition method based on the preparation of a dry impregnation aqueous solution comprising ammonia in all its forms (gas or in solution, preferably in aqueous solution) and a complexing agent, followed by aging of the aqueous solution prior to dry impregnation of the support, maturation of the impregnated support, drying and calcination. This method notably allows to obtain a homogenous distribution of the group VIII metal over the entire ball.

BACKGROUND OF THE INVENTION

Many patents deal with the dehydrogenation of long chain-paraffins. They generally provide means for limiting side reactions that focus on the process and/or on the catalytic formulation.

Thus, the great majority of the patents that deal with long chain paraffin dehydrogenation are concerned with the addition of hydrogen to the feed for $H_2$/hydrocarbons molar ratios ranging between 1 and 10 (EP-0,462,094 B1). The purpose of this make-up hydrogen is to limit or to retard coke formation at the catalyst surface without too negative an effect on the conversion of the n-paraffins being observed. In patent EP-0, 462,094 B1, the choice has been made of working at a lower temperature (<450° C.) and with lower $H_2$/HC molar ratios ranging between 0.5 and 1.9. Another solution provided by U.S. Pat. No. 3,448,165, U.S. Pat. No. 3,907,921 and U.S. Pat. No. 5,233,118 consists in injecting a small amount of water and/or of sulfur with the hydrocarbon feed to be dehydrogenated. The water can be injected at constant flow rate or at a flow rate that increases gradually with the operating time of the catalyst. It has been reported that optimum performance was obtained by increasing the injection of water with the temperature of the reactor during the working cycle.

As regards the formulation, U.S. Pat. No. 4,716,143 discloses a catalyst based on supported platinum such that the platinum distribution is limited to the outer surface of the support over a maximum thickness of 400 µm. The advantage of such a choice lies in that a distribution over the periphery of the support decreases parasitic reactions and, consequently, improves the catalyst performances. However, this type of distribution only rarely allows one to obtain homogeneous platinum/modifier atomic ratios on the particle scale (nanometer). Examples of the most commonly used platinum modifiers are group IIIA and group IVA elements, in particular tin (U.S. Pat. No. 3,745,112). The role of the tin predominantly present at the catalyst surface in an oxidation state of +2 and/or +4 is to modify the properties of the Pt particles, which allows to increase the catalyst selectivity and stability (by hydrogenolysis reduction for example). Tin also has an impact on the acidic properties of the support. Another example of a platinum modifier is indium, notably mentioned in U.S. Pat. No. 4,551,574, EP-B-183,861 and JP-B-91,041, 211. In fact, the latter confers better stability while also inhibiting the side reactions of deep dehydrogenation (polyolefins) and of skeleton isomerization (branched hydrocarbons).

In order to limit side reactions, it is interesting to deposit an alkali or alkaline-earth metal whose role consists in taking part in the neutralization of the acid sites of the support of low and medium strength. Thus, even limited addition of lithium (0.1 wt. %) allows to neutralize these acid sites responsible for the formation of isomerized and light products (cracking reactions). Aromatics formation can also be decreased through lithium addition. However, it is also known that this addition leads to a decrease in the total activity of the catalyst. This decrease is often linked with a phenomenon of metallic phase coverage by the alkali metal.

As for preparation, U.S. Pat. No. 5,482,910 describes a catalyst preparation method that involves using a chelating ligand such as EDTA. An aqueous solution comprising the chelating ligand and a salt of an alkali or alkaline-earth metal is first prepared at a temperature ranging from about 80° C. to the boiling point temperature thereof. This solution is then mixed with a solution comprising a group VIII metal. This solution is aged at a temperature ranging between about 40° C. and 100° C., then it is used for impregnating the support. The impregnated support is thereafter dried, calcined, optionally oxychlorinated and finally reduced.

U.S. Pat. No. 3,259,589 describes a catalyst preparation method comprising preferably platinum preferably deposited on an alumina. The platinum can be introduced in complexed form by an organic acid of HOOC[CRR']n COOH type, with R=OH, H or an alkyl function and R'=H, an alkyl function or COOH.

U.S. Pat. No. 2,889,287 describes a hydrocracking catalyst preparation method comprising at least one active metal selected from the group consisting of groups VI and VIII metals of the periodic table and the oxides of said metals, a support selected from the group consisting of alumina and silica-alumina. The active metal(s) is (are) deposited on the support by impregnation of the support with a complex of the metal(s), then the impregnated support is dried and calcined.

SUMMARY OF THE INVENTION

The invention relates to a method of preparing a dehydrogenation catalyst comprising a group VIII metal, a group IVA metal and a refractory oxide support. The method comprises stages of preparing the dry impregnation aqueous solution containing said group VIII metal, ammonia, either in solution or in gas form, and a complexing agent. It then comprises stages of aging the aqueous solution, of dry impregnation of the support, of maturing the impregnated support, of drying the impregnated support and of calcining the dried support.

DETAILED DESCRIPTION

The invention relates to a method of preparing a dehydrogenation catalyst comprising a group VIII metal, a group IVA metal, a refractory oxide support of specific surface area ranging between 10 and 250 m$^2$/g and optionally at least one alkali or alkaline-earth metal in cases where the specific surface area of the support ranges between 10 and 175 m$^2$/g, at least one alkali or alkaline-earth metal in cases where the specific surface area of the support ranges between 175 and 250 m$^2$/g, said method comprising the following stages:

a stage a) of preparing the dry impregnation aqueous solution, comprising said group VIII metal, ammonia, either in solution, preferably in aqueous solution, or in gas form, and a complexing agent selected from the group made up of EDTA and derivatives thereof, at least bidentate primary amine complexes, secondary amine complexes, pyridine ring derivatives, preferably selected from the group made up of DTPA and derivatives thereof, ethylene diamine, cyclen and 2,2'-bipyridine, a stage b) of aging the aqueous solution obtained at the end of stage a), over a period of time ranging between 5 minutes and 24 hours, preferably between 5 minutes and 12 hours, at a temperature ranging between 15° C. and 100° C., a stage c) of dry impregnation of said support by the aqueous solution obtained at the end of stage b), a stage d) of maturing the impregnated support obtained at the end of stage c), said maturation being carried out in a humid medium over a period of time ranging between 30 minutes and 48 hours, preferably between 1 hour and 36 hours, a stage e) of drying the impregnated support obtained at the end of stage d), the drying temperature ranging between 80° C. and 200° C., preferably between 100° C. and 150° C., over a period of time ranging between 5 minutes and 5 days, a stage f) of calcining the dried support obtained at the end of stage e), the calcination temperature ranging between 300° C. and 850° C. and the calcination time ranging between 5 minutes and 20 hours, preferably between 20 minutes and 16 hours.

The group IVA metal can be introduced using any method known to the person skilled in the art such as, for example, excess impregnation, dry impregnation or upon preparation of the support. Within the scope of this invention, it is particularly interesting to introduce it upon preparation of the support.

The catalyst can also comprise an alkali or alkaline-earth metal. The alkali metal preferably is lithium.

In the case of a support of specific surface area ranging between 10 and 175 m$^2$/g, preferably between 20 and 150 m$^2$/g, more preferably between 20 and 140 m$^2$/g, the presence of an alkali or alkaline-earth metal in the catalyst is not necessary. Preferably, the catalyst comprises no alkali or alkaline-earth metal in this case.

In the case of a support with a specific surface area ranging between 175 and 250 m$^2$/g, preferably between 150 and 250 m$^2$/g, more preferably between 140 and 240 m$^2$/g, the presence of an alkali or alkaline-earth metal in the catalyst is obligatory.

In the case of catalysts comprising at least one alkali or alkaline-earth metal, the latter can be introduced by means of any method known to the person skilled in the art such as, for example, excess impregnation, dry impregnation or upon preparation of the support. Within the scope of this invention, it is particularly interesting to introduce them by dry impregnation.

The group VIII metal can be introduced in form of metallic salt, hydroxide, oxide, halogenated and/or hydrated. Preferably, this metal is platinum. In cases where the noble metal is platinum, the platinum precursors belong to the following group, without this list being imitative: hexachloroplatinic acid, bromoplatinic acid, ammonium chloroplatinate, platinum chlorides, platinum dichlorocarbonyl dichloride, tetraamine platinum chloride. Organic platinum complexes such as platinum diacetylacetonate (II) can also be used. Preferably, the precursor used is hexachloroplatinic acid.

For stage c), the support of pore volume Vp is generally contacted with a volume V of the aged dry impregnation aqueous solution obtained at the end of stage b), while having $0.9Vp < V < 1.1Vp$.

The pore volume is defined as the volume of the pores whose size is above 0.0036 μm. It can for example be measured by mercury porosimetry.

For stage d), maturation in a humid medium corresponds to a maturation stage in a medium whose relative humidity is above 80%. Relative humidity is defined as the ratio of the partial pressure of the steam contained in the air to the saturated vapour pressure at the same temperature and pressure.

According to a variant, the method further comprises, after f), a stage g) of catalyst reduction under hydrogen at a temperature ranging between 300° C. and 850° C. over a period of time ranging between 5 minutes and 20 hours, preferably between 20 minutes and 16 hours.

The final proportion of group VIII metal in the catalyst generally ranges between 0.01 and 0.5 wt. %, preferably between 0.05 and 0.35 wt. %.

The final proportion of group IVA metal in the catalyst generally ranges between 0.02 and 0.5 wt. %, preferably between 0.05 and 0.35 wt. %. The final proportion of alkali or alkaline-earth metal generally ranges between 0 and 3 wt. %, preferably between 0 and 1 wt. %.

According to a variant, the support further comprises at least one doping metal selected from the group made up of scandium, yttrium, germanium, indium, antimony, lead, thallium, gallium, bismuth, phosphorus, arsenic, lanthanides and actinides, preferably selected from the group made up of germanium, indium, antimony, lead, thallium and phosphorus. In the case of the dopants, precursors of nitrate, halogenide or organometallic type can be used, without this list being limitative.

Generally, the support of the catalysts prepared is a refractory oxide selected from among magnesium, titanium, zirconium, alumina, silicon oxides or mixtures thereof. Preferably, silica, alumina or silica-alumina, and more preferably alumina are used. Besides, the specific surface area of the support generally ranges between 10 and 250 $m^2/g$, preferably between 15 and 175 $m^2/g$ or even between 20 and 150 $m^2/g$.

The catalysts prepared according to the invention generally have a homogenous platinum distribution. Platinum generally has a distribution coefficient R ranging between 0.80 and less than 1.2. In fact, in order to limit diffusion limitations, metallic deposition on the outer surface of the support is preferably used. However, this type of distribution rarely allows to obtain homogeneous platinum to modifier atomic ratios on the particle scale (of the order of one nanometer). Furthermore, an active phase overconcentration at the surface can generate diffusion limitations at the level of the catalyst grain (extragranular diffusion) and therefore reduce the overall reaction efficiency.

Definition of Coefficient R

The distribution profiles of the elements within the catalyst grains are obtained by means of an EPMA. It is thus possible to obtain the distribution profile c(x) for x∈[−r;+r] the local concentration of the element, r the radius of the ball or of the extrudate and x the position of the analysis point along the diameter of the grain with respect to the centre of this grain.

The distribution of the elements is characterized by a dimensionless coefficient R weighting the local concentration by an increasing weight as a function of the position on the diameter. By definition:

$$R = \int_{-r}^{r} c(x)x^2 dx \Big/ \frac{r^2}{3} \int_{-r}^{r} c(x) dx$$

Thus, an element whose concentration is uniform has a coefficient R equal to 1, an element deposited in a dome (concentration at the core higher than the concentration at the edges of the support) has a coefficient above 1 and an element distributed in a crust (concentration at the edges higher than the concentration at the core of the support) has a coefficient below 1. Analysis using an EPMA gives the concentration values in a finite number of values of x, R is thus evaluated numerically by integration methods known to the person skilled in the art. Preferably, R is determined by means of the trapezoidal method.

The invention also relates to a dehydrogenation method carried out in vapour phase under hydrogen by contacting a catalyst prepared according to the invention on a feed, said feed comprising paraffins having 8 to 22 carbon atoms, preferably 10 to 22 carbon atoms and more preferably 10 to 14 carbon atoms, the $H_2$/feed molar ratio ranging between 0.5 and 10, preferably between 4 and 8, the temperature ranging between 300° C. and 800° C., preferably between 400° C. and 550° C., and more preferably between 450° C. and 520° C., the total pressure ranging between 0.01 and 2 MPa, preferably between 0.1 and 1 MPa, and more preferably between 0.1 and 0.5 MPa, the hourly space velocity (expressed in liter of feed per liter of catalyst and per hour) ranging between 0.5 and 300 $h^{-1}$, preferably between 1 and 100 $h^{-1}$, and more preferably between 10 and 50 $h^{-1}$.

The paraffins of the feed to be treated are preferably linear. However, the method according to the invention also applies to the dehydrogenation of a feed containing linear paraffins and branched paraffins, the branched paraffins representing less than 50 wt. % of the linear paraffins. Water is advantageously added to the feed to be dehydrogenated.

The dehydrogenation method according to the invention is advantageously implemented in a fixed-bed unit. The catalyst can be reduced ex situ or in situ under hydrogen at a temperature ranging between 400° C. and 500° C.

EXAMPLES

Example 1 (not in Accordance)

Preparation of Catalyst A

The support is an alumina of specific surface area 215 $m^2$ per gram containing 0.3 wt. % tin.

100 g support are contacted with 500 $cm^3$ of an aqueous solution of hydrochloric acid and of hexachloroplatinic acid comprising 0.30 g platinum. The catalyst is then dried at 120° C. for 1 hour, calcined at 500° C. for 2 hours in dry air. This stage is followed by calcination at 500° C. for 2 hours in humid air prior to impregnation of 0.2 wt. % lithium. The catalyst thus obtained is aged for 24 hours in a humid atmosphere (relative humidity 99%), dried 1 hour at 120° C., calcined for 2 hours at 500° C. and reduced under hydrogen for 2 hours at 450° C.

The final catalyst contains 0.29 wt. % platinum, 0.3 wt. % tin and 0.2 wt. % lithium. The platinum has an average distribution coefficient of 0.99.

Example 2 (not in Accordance)

Preparation of Catalyst B

The support is an alumina of specific surface area 215 $m^2$ per gram containing 0.3 wt. % tin.

100 g support are contacted with 65 $cm^3$ of an aqueous solution of hydrochloric acid and of hexachloroplatinic acid comprising 0.30 g platinum. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidity 99%), dried 1 hour at 120° C., calcined for 2 hours at 500° C. and reduced under hydrogen 2 hours at 450° C.

The final catalyst contains 0.29 wt. % platinum, 0.3 wt. % tin and 0.2 wt. % lithium. The platinum has an average distribution coefficient of 0.61.

Example 3 (not in Accordance)

Preparation of Catalyst C

The support is an alumina of specific surface area 215 m² per gram containing 0.3 wt. % tin.

100 g support are contacted with 65 cm³ of an aqueous solution of hexachloroplatinic acid comprising 0.30 g platinum. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidity 99%), dried 1 hour at 120° C., calcined for 2 hours at 50° C. and reduced under hydrogen 2 hours at 450° C.

The final catalyst contains 0.29 wt. % platinum, 0.3 wt. % tin and 0.2 wt. % lithium. The platinum has an average distribution coefficient of 0.65.

Example 4 (not in Accordance)

Preparation of Catalyst D

The support is an alumina of specific surface area 215 m² per gram containing 0.3 wt. % tin.

100 g support are contacted with 65 cm³ of an aqueous solution of hexachloroplatinic acid comprising 0.30 g platinum and 2 molar equivalents of citric acid with respect to the platinum. This solution has first been aged for 3 hours in the presence of ammonia. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidity 99%), dried 1 hour at 120° C., calcined for 2 hours at 500° C. and reduced under hydrogen 2 hours at 450° C.

The final catalyst contains 0.29 wt. % platinum, 0.3 wt. % tin and 0.2 wt. % lithium. The platinum has an average distribution coefficient of 0.78.

The use of citric acid for catalyst D does not allow to obtain a well-distributed catalyst.

Example 5 (not in Accordance)

Preparation of Catalyst E

The support is an alumina of specific surface area 215 m² per gram containing 0.3 wt. % tin.

100 g support are contacted with 65 cm³ of an aqueous solution of hexachloroplatinic acid comprising 0.30 g platinum. This solution has been aged for 3 hours in the presence of ammonia. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidity 99%), dried 1 hour at 120° C., calcined for 2 hours at 500° C. and reduced under hydrogen 2 hours at 450° C.

The final catalyst contains 0.29 wt. % platinum, 0.3 wt. % tin and 0.2 wt. % lithium. The platinum has an average distribution coefficient of 0.88.

Example 6 (in Accordance)

Preparation of Catalyst F

The support is an alumina of specific surface area 215 m² per gram containing 0.3 wt. % tin.

100 g support are contacted with 65 cm³ of an aqueous solution of hexachloroplatinic acid comprising 0.30 g platinum and 3 molar equivalents of ethylene diamine with respect to the platinum. This solution has first been aged for 3 hours in the presence of ammonia. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidity 99%), dried 1 hour at 120° C., calcined for 2 hours at 500° C. and reduced under hydrogen 2 hours at 450° C.

The final catalyst contains 0.29 wt. % platinum, 0.3 wt. % tin and 0.2 wt. % lithium. The platinum has an average distribution coefficient of 0.97.

Example 7 (not in Accordance)

Preparation of Catalyst G

The support is an alumina of specific surface area 215 m² per gram containing 0.3 wt. % tin.

100 g support are contacted with 65 cm³ of an aqueous solution of hexachloroplatinic acid comprising 0.30 g platinum and 3 molar equivalents of ethylene diamine with respect to the platinum. This solution has first been aged for 3 hours in the presence of ammonia. The catalyst thus obtained is not aged in a humid atmosphere but it is dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidity 99%), dried 1 hour at 120° C., calcined for 2 hours at 500° C. and reduced under hydrogen 2 hours at 450° C.

The final catalyst contains 0.29 wt. % platinum, 0.3 wt. % tin and 0.2 wt. % lithium. The platinum has an average distribution coefficient of 0.87.

Example 8 (not in Accordance)

Preparation of Catalyst H

The support is an alumina of specific surface area 215 m² per gram containing 0.3 wt. % tin.

100 g support are contacted with 65 cm³ of an aqueous solution of hexachloroplatinic acid comprising 0.30 g platinum and 3 molar equivalents of ethylene diamine with respect to the platinum. This solution has not first been aged for 3 hours in the presence of ammonia. The solution comes in form of a suspension. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidify 99%), dried 1 hour at 120° C., calcined for 2 hours at 500° C. and reduced under hydrogen 2 hours at 450° C.

The final catalyst contains 0.29 wt. % platinum, 0.3 wt. % tin and 0.2 wt. % lithium. The platinum has an average distribution coefficient of 0.68.

Example 9 (in Accordance)

Preparation of Catalyst I

The support is an alumina of specific surface area 215 m² per gram containing 0.3 wt. % tin.

100 g support are contacted with 65 cm³ of an aqueous solution of hexachloroplatinic acid comprising 0.30 g platinum and 1 molar equivalent of diethylene triamine penta-acetic acid (DTPA) with respect to the platinum. This solution has first been aged for 3 hours in the presence of ammonia. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidity 99%), dried 1 hour at 120° C., calcined for 2 hours at 500° C. and reduced under hydrogen 2 hours at 450° C.

The final catalyst contains 0.29 wt. % platinum, 0.3 wt. % tin and 0.2 wt. % lithium. The platinum has an average distribution coefficient of 0.92.

Example 10 (in Accordance)

Preparation of Catalyst J

The support is an alumina of specific surface area 215 m² per gram containing 0.3 wt. % tin.

100 g support are contacted with 65 cm³ of an aqueous solution of hexachloroplatinic acid comprising 0.30 g platinum and 3 molar equivalents of 2,2'-bipyridyl with respect to the platinum. This solution has first been aged for 3 hours in the presence of ammonia. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged 24 hours in a humid atmosphere (relative humidify 99%), dried 1 hour at 120° C., calcined for 2 hours at 500° C. and reduced under hydrogen 2 hours at 450° C.

The final catalyst contains 0.29 wt. % platinum, 0.3 wt. % fin and 0.2 wt. % lithium. The platinum has an average distribution coefficient of 0.85.

Example 11 (in Accordance)

Preparation of Catalyst K

The support is an alumina of specific surface area 40 m² per gram containing 0.11 wt. % tin.

100 g support are contacted with a volume of aqueous solution of hexachloroplatinic acid equivalent to the pore volume of the support, with 1 molar equivalent of diethylene triamine penta-acetic acid (DTPA) with respect to the platinum so as to deposit 0.11 wt. % platinum. This solution has first been aged for 3 hours in the presence of ammonia. The catalyst thus obtained is aged for 24 hours in a humid atmosphere (relative humidity 99%), then dried for 1 hour at 120° C., calcined for 2 hours at 500° C. in ambient air prior to being reduced under hydrogen for 2 hours at 450° C.

The final catalyst contains 0.11 wt. % platinum and 0.11 wt. % tin. The platinum has an average distribution coefficient of 0.94.

Example 12 (in Accordance)

Preparation of Catalyst L

The support is an alumina of specific surface area 215 m² per gram containing 0.3 wt. % tin.

100 g support are contacted with 65 cm³ of an aqueous solution of hexachloroplatinic acid comprising 0.30 g platinum and 1 molar equivalent of diethylene triamine penta-acetic acid (DTPA) with respect to the platinum. This solution has first been aged for 3 hours in the presence of ammonia. The catalyst thus obtained is aged for 24 hours in a humid atmosphere (relative humidity 99%), then dried for 1 hour at 120° C., calcined for 2 hours at 500° C. in dry air prior to being reduced under hydrogen for 2 hours at 450° C.

The final catalyst contains 0.29 wt. % platinum and 0.3 wt. % tin. The platinum has an average distribution coefficient of 0.92.

Example 13 (in Accordance)

Preparation of Catalyst M

The support is an alumina of specific surface area 40 m² per gram containing 0.11 wt. % tin.

100 g support are contacted with a volume of aqueous solution of hexachloroplatinic acid equivalent to the pore volume of the support, with 1 molar equivalent of diethylene triamine penta-acetic acid (DTPA) with respect to the platinum so as to deposit 0.11 wt. % platinum. This solution has first been aged for 3 hours in the presence of ammonia. The catalyst thus obtained is aged for 24 hours in a humid atmosphere (relative humidity 99%), then dried for 1 hour at 120° C., calcined for 2 hours at 500° C. in ambient air. This catalyst is then impregnated with 0.05 wt. % lithium. The catalyst thus obtained is aged for 24 hours in a humid atmosphere (relative humidity 99%), dried for 1 hour at 120° C., calcined for 2 hours at 500° C. and reduced under hydrogen for 2 hours at 450° C.

The final catalyst contains 0.11 wt. % platinum, 0.11 wt. % tin and 0.05 wt. % lithium. The platinum has an average distribution coefficient of 0.95.

Example 14 (in Accordance)

Preparation of Catalyst N

The support is an alumina of specific surface area 215 m² per gram containing 0.3 wt. % tin.

100 g support are contacted with 65 cm³ of an aqueous solution of hexachloroplatinic acid comprising 0.30 g platinum and 1 molar equivalent of cyclen (1,4,7,10-tetra-azacyclododecane) with respect to the platinum. This solution has first been aged for 3 hours in the presence of ammonia. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged for 24 hours in a humid atmosphere (relative humidity 99%), dried for 1 hour at 120° C., calcined for 2 hours at 500° C. and reduced under hydrogen for 2 hours at 450° C.

The final catalyst contains 0.29 wt. % platinum, 0.3 wt. % tin and 0.2 wt. % lithium. The platinum has an average distribution coefficient of 0.98.

Example 15 (in Accordance)

Preparation of Catalyst O

The support is an alumina of specific surface area 215 m² per gram containing 0.3 wt. % tin.

100 g support are contacted with 65 cm³ of an aqueous solution of hexachloroplatinic acid comprising 0.30 g platinum and 3 molar equivalents of ethylene diamine with respect to the platinum. This solution has first been aged for 3 hours in the presence of ammonia. 2.8 g trichloroacetic acid is added to the preparation. The catalyst thus obtained is aged for 24 hours in a humid atmosphere (relative humidity 99%), then dried for 1 hour at 120° C., calcined for 2 hours at 500° C. in dry air prior to being calcined for 2 hours at 500° C. in humid air. This catalyst is then impregnated with 0.2 wt. % lithium. The catalyst thus obtained is aged for 24 hours in a humid atmosphere (relative humidity 99%), dried for 1 hour at 120° C., calcined for 2 hours at 500° C. and reduced under hydrogen for 2 hours at 450° C.

The final catalyst contains 0.29 wt. % platinum, 0.3 wt. % tin and 0.2 wt. % lithium. The platinum has an average distribution coefficient of 1.

Example 16

Catalytic Tests

The catalysts for which platinum has an average distribution coefficient above 0.80 were tested. It is in fact known to the person skilled in the art that dehydrogenation catalysts have to be well distributed for lack of homogeneous distribution of the metals in one crust. In particular, the use of citric acid for catalyst D does not allow to obtain a well-distributed catalyst.

The catalysts selected are subjected to an n-dodecane dehydrogenation test carried out in an isothermal tubular reactor. 2 g catalyst are reduced at 450° C. for 2 hours at a flow rate of 4 liters hydrogen per hour. The operating conditions are as follows:

feed: n-dodecane addition of 1500 ppm by weight water in relation to the feed temperature: 460° C.

pressure: 0.27 MPa $H_2/nC_{12}$ (molar): 6 mass ratio liquid $nC_{12}$/catalyst mass: 40 h$^{-1}$ samples are taken and analysed after 100 hours reaction.

The results obtained under such conditions are given in the table hereafter. The $nC_{12}$ conversion and yield values are expressed in wt. % in relation to the feed.

TABLE 1

Characteristics and n-dodecane dehydrogenation performances of the catalysts after 100 hours test

| Catalyst | BET surface area (in m²/g) | Lithium | Conversion (%) n-C12 | Yield (%) C12 olefins | Yield (%) C12 aromatics |
|---|---|---|---|---|---|
| A (not in accordance) | 215 | Yes | 10.2 | 9.1 | 0.32 |
| E (not in accordance) | 215 | Yes | 9.9 | 8.7 | 0.35 |
| F (in accordance) | 215 | Yes | 10.3 | 9.3 | 0.31 |
| G (not in accordance) | 215 | Yes | 10.0 | 8.7 | 0.31 |
| I (in accordance) | 215 | Yes | 10.1 | 9.2 | 0.33 |
| J (in accordance) | 215 | Yes | 10.1 | 9.2 | 0.31 |
| K (in accordance) | 40 | No | 10.4 | 9.5 | 0:25 |
| L (not in accordance) | 215 | No | 11.3 | 8.1 | 0.81 |
| M (in accordance) | 40 | Yes | 10.4 | 9.6 | 0.21 |
| N (in accordance) | 215 | Yes | 10.3 | 9.4 | 0.30 |
| O (in accordance) | 215 | yes | 10.4 | 9.5 | 0.31 |

Table 1 describes the catalytic performances of the well-distributed catalysts (average distribution coefficient ranging between 0.8 and 1.2).

The catalytic performances are equivalent for the dry impregnation preparation method according to the invention and for the excess impregnation preparation method (catalyst A). Thus, changing for dry impregnation is, on the one hand, more economical and, on the other hand, it does not alter the catalytic performances.

Comparison of the various Pt/Sn catalysts prepared by dry impregnation shows that the use of ammonia alone, without a complexing agent, followed by the aging stage in a humid medium (catalyst E), the use of ammonia with a complexing agent but without the aging stage in a humid medium (catalyst G) and the use of a complexing agent alone, without ammonia, followed by the aging stage in a humid medium (catalyst H) does not allow to obtain interesting performances in combination with a good metal distribution (average distribution coefficient ranging between 0.8 and 1.2).

On the other hand, the use of ammonia and of an aging stage in a humid medium in combination with the complexing agents according to the invention allows to obtain well-distributed catalysts and more interesting performances (catalysts F, I, J, K, M, N and O).

Besides, the use of citric acid in the presence of ammonia, followed by the aging stage in a humid atmosphere, does not allow to obtain a catalyst whose metals are well distributed (catalyst D).

Examples K and M show that the use of a support with a specific surface area of 40 m²/g allows to do without the lithium deposition stage in contrast with examples I and L with 215 m²/g.

The preceding examples can be repeated with similar success by substituting the generically or specifically described reactants and/or operating conditions of this invention for those used in the preceding examples.

In the foregoing and in the examples and, all parts and percentages are by weight, unless otherwise indicated.

The entire disclosures of all applications, patents and publications, cited herein and of corresponding FR application Ser. No. 09/02.261, filed May 7, 2009. are incorporated by reference herein.

The invention claimed is:

1. A method of preparing a dehydrogenation catalyst comprising a group VIII metal, a group IVA metal, a refractory oxide support of specific surface area ranging between 10 and 250 m$^2$/g, at least one alkali or alkaline-earth metal in cases where the specific surface area of the support ranges between 175 and 250 m$^2$/g, and optionally where the specific surface area of the support ranges between 10 and 175 m$^2$/g, said method comprising the following stages:
  a stage a) of preparing a dry impregnation aqueous solution comprising said group VIII metal, ammonia, either in solution or in gas form, and a complexing agent selected from EDTA and derivatives thereof, at least bidentate primary amine complexes, secondary amine complexes, and pyridine ring derivatives,
  a stage b) of aging said dry impregnation aqueous solution obtained at the end of stage a), over a period of time ranging between 5 minutes and 24 hours, at a temperature ranging between 15° C. and 100° C.,
  a stage c) of dry impregnation of said refractory oxide support by said aqueous solution obtained at the end of stage b) to obtain an impregnated support,
  a stage d) of maturing said impregnated support obtained at the end of stage c), said maturation being carried out in a humid medium over a period of time ranging between 30 minutes and 48 hours,
  a stage e) of drying the matured, impregnated support obtained at the end of stage d), the drying temperature ranging between 80° C. and 200° C., over a period of time ranging between 5 minutes and 5 days,
  a stage f) of calcining the dried, matured, impregnated support obtained at the end of stage e), the calcination temperature ranging between 300° C. and 850° C. and the calcination time ranging between 5 minutes and 20 hours.

2. The method according to claim 1, further comprising, after stage f), a stage g) of catalyst reduction under hydrogen at a temperature ranging between 300° C. and 850° C. over a period of time ranging between 5 minutes and 20 hours.

3. The method according to claim 1, further, wherein the final proportion of group VIII metal in the catalyst ranges between 0.01 and 0.5 wt. %.

4. The method according to claim 1, wherein the group VIII metal is platinum.

5. The method according to claim 1, wherein the final proportion of group IVA metal in the catalyst ranges between 0.02 and 0.5 wt. %.

6. The method according to claim 1, wherein the group IVA metal is tin.

7. The method according to claim 1, wherein the final proportion of alkali or alkaline-earth metal ranges between 0 and 3 wt. %.

8. The method according to claim 1, wherein said at least one alkali metal or alkaline earth metal is lithium which is included in the catalyst.

9. The method according to claim 1, wherein the refractory support further comprises at least one doping metal selected from scandium, yttrium, germanium, indium, antimony, lead, thallium, gallium, bismuth, phosphorus, arsenic, lanthanides and actinides.

10. The method according to claim 1, wherein the complexing agent is selected from DTPA and derivatives thereof, ethylene diamine, cyclen and 2,2'-bipyridine.

11. The method according to claim 1, wherein the specific surface area of the support ranges between 10 and 175 m$^2$/g.

12. The method according to claim 11, wherein the catalyst comprises no alkali or alkaline-earth metal.

13. The method according to claim 4, wherein the group IVA metal is tin.

14. The method according to claim 4, wherein said at least one alkali metal or alkali earth metal is lithium which is included in the catalyst.

15. The method according to claim 13, wherein said at least one alkali metal or alkali earth metal is lithium which is included in the catalyst.

16. The method according to claim 15, wherein the refractory support further comprises at least one doping metal selected from scandium, yttrium, germanium, indium, antimony, lead, thallium, gallium, bismuth, phosphorus, arsenic, lanthanides and actinides.

17. The method according to claim 13, wherein the complexing agent is selected from DTPA and derivatives thereof, ethylene diamine, cyclen and 2,2'-bipyridine.

18. The method according to claim 15, wherein the complexing agent is selected from DTPA and derivatives thereof, ethylene diamine, cyclen and 2,2'-bipyridine.

19. The method according to claim 16, wherein the complexing agent is selected from DTPA and derivatives thereof, ethylene diamine, cyclen and 2,2'-bipyridine.

20. The method according to claim 1, wherein the complexing agent selected from EDTA, DTPA, ethylene diamine, cyclen and 2,2'-bipyridine, the final proportion of group VIII metal in the catalyst ranges between 0.01 and 0.5 wt. %, the final proportion of group IVA metal in the catalyst ranges between 0.02 and 0.5 wt. %, and the final proportion of alkali or alkaline-earth metal ranges between 0 and 3 wt. %.

21. The method according to claim 1, wherein the group VIII metal is platinum, the group IVA metal is tin, and the at least one alkali metal or alkali earth metal, if present, is lithium.

* * * * *